US008790237B2

(12) United States Patent
Vermeiren

(10) Patent No.: US 8,790,237 B2
(45) Date of Patent: Jul. 29, 2014

(54) MECHANICAL STIMULATOR HAVING A QUICK-CONNECTOR

(75) Inventor: Jan Vermeiren, Boechout (BE)

(73) Assignee: Cochlear Limited, Macquarie University, NSW (AU)

( * ) Notice: Subject to any disclaimer, the term of this patent is extended or adjusted under 35 U.S.C. 154(b) by 370 days.

(21) Appl. No.: 13/048,680

(22) Filed: Mar. 15, 2011

(65) Prior Publication Data

US 2012/0239113 A1 Sep. 20, 2012

(51) Int. Cl.
*H04R 25/00* (2006.01)
*A61N 1/36* (2006.01)

(52) U.S. Cl.
CPC .......... *H04R 25/606* (2013.01); *A61N 1/36032* (2013.01)
USPC .............................................. 600/25; 607/57

(58) Field of Classification Search
None
See application file for complete search history.

(56) References Cited

U.S. PATENT DOCUMENTS

| | | | | |
|---|---|---|---|---|
| 3,508,538 | A * | 4/1970 | Keller, Jr. | 600/510 |
| 5,275,620 | A * | 1/1994 | Darby et al. | 607/1 |
| 6,293,903 | B1 | 9/2001 | Kasic, II et al. | |
| 6,482,144 | B1 | 11/2002 | Müller | |
| 6,491,622 | B1 | 12/2002 | Kasic, II et al. | |
| 6,517,476 | B1 | 2/2003 | Bedoya et al. | |
| 6,537,199 | B1 | 3/2003 | Muller et al. | |
| 6,540,661 | B1 * | 4/2003 | Muller | 600/25 |
| 6,579,317 | B2 | 6/2003 | Kurz | |
| 6,705,985 | B2 | 3/2004 | Easter et al. | |
| 6,945,999 | B2 | 9/2005 | Schneider et al. | |
| 7,153,257 | B2 | 12/2006 | Schneider et al. | |
| 7,160,244 | B2 * | 1/2007 | Westerkull | 600/25 |
| 7,166,069 | B2 | 1/2007 | Schneider et al. | |
| 7,186,211 | B2 | 3/2007 | Schneider et al. | |
| 7,204,800 | B2 | 4/2007 | Easter et al. | |
| 7,278,963 | B2 | 10/2007 | Schneider et al. | |
| 7,468,028 | B2 | 12/2008 | Schneider et al. | |
| 7,582,052 | B2 | 9/2009 | Waldmann | |
| 7,722,525 | B2 | 5/2010 | Andrews | |
| 2002/0147429 | A1 * | 10/2002 | Cowan et al. | 604/187 |
| 2004/0133065 | A1 * | 7/2004 | Easter et al. | 600/25 |
| 2005/0157899 | A1 * | 7/2005 | Raviv et al. | 381/322 |
| 2005/0225180 | A1 | 10/2005 | Schneider et al. | |
| 2007/0055092 | A1 | 3/2007 | Easter et al. | |

(Continued)

FOREIGN PATENT DOCUMENTS

| | | | |
|---|---|---|---|
| KR | 20-0449881 | | 8/2010 |
| WO | 97/30565 | A1 | 8/1997 |
| WO | 97/36457 | A1 | 10/1997 |
| WO | WO 2008/051848 | A2 | 5/2008 |

OTHER PUBLICATIONS

Traynor et al., The Future is Here: The Otologics Fully Implantable Hearing System, AudiologyOnline, Nov. 19, 2007, http://www.audiologyonline.com/articles/pf_article_detail.asp?article_id=1903.

(Continued)

*Primary Examiner* — Kennedy Schaetzle
(74) *Attorney, Agent, or Firm* — K&L Gates, LLP

(57) ABSTRACT

An implantable hearing prosthesis comprising a vibrator for generating vibrations, a coupling arm adapted to be attached to an element of a recipient's ear; and a quick-connector comprising a first connector half disposed on the vibrator and a second connector half disposed on the coupling arm, wherein the connector halves are adapted to be releasably mated with one another to secure the coupling arm in relative position to the vibrator.

17 Claims, 13 Drawing Sheets

(56) References Cited

U.S. PATENT DOCUMENTS

| | | | | |
|---|---|---|---|---|
| 2008/0004486 | A1 | 1/2008 | Andrews et al. | |
| 2008/0051623 | A1 | 2/2008 | Schneider et al. | |
| 2009/0124849 | A1 | 5/2009 | Pergola | |
| 2009/0149697 | A1 | 6/2009 | Steinhardt et al. | |
| 2009/0248156 | A1 | 10/2009 | Pizzoli et al. | |
| 2009/0259091 | A1 | 10/2009 | Parker | |
| 2009/0306458 | A1* | 12/2009 | Parker et al. | 600/25 |
| 2010/0042119 | A1 | 2/2010 | Simms et al. | |
| 2010/0324355 | A1* | 12/2010 | Spitaels et al. | 600/25 |
| 2012/0040548 | A1* | 2/2012 | King | 439/341 |
| 2012/0088956 | A1* | 4/2012 | Asnes et al. | 600/25 |
| 2012/0197066 | A1* | 8/2012 | Abel et al. | 600/25 |
| 2012/0302823 | A1* | 11/2012 | Andersson et al. | 600/25 |

OTHER PUBLICATIONS

International Search Report and Written Opinion for International Application No. PCT/IB2012/051188 mailed Sep. 24, 2012 (11 pages).

* cited by examiner

MECHANICAL STIMULATOR HAVING A QUICK-CONNECTOR

BACKGROUND

1. Field of the Invention

The present invention relates generally to a hearing prosthesis, and more particularly, to a mechanical stimulator having a quick-connector.

2. Related Art

Implantable hearing prostheses generally fall into one of several categories, including devices used to treat sensorineural hearing loss, devices used to treat conductive hearing loss, and devices used to treat mixed hearing loss (that is, a combination of conductive and sensorineural hearing loss). Certain hearing prosthesis include an implantable actuator that used to treat various types of hearing loss.

One exemplary hearing prosthesis that includes an implantable actuator is a mechanical stimulator. In this arrangement, the actuator is coupled to an element of a recipient's ear, such as the middle ear bones, inner ear or semicircular canal. In operation, the actuator vibrates in response to electrical signals based on a received sound. The vibrations of the actuator are delivered to the ear element via a coupling arm.

An implantable actuator may be used as sound pickup device in hearing prosthesis such as mechanical stimulators, cochlear implants, etc. In such an arrangement, the actuator functions as an implantable microphone that converts vibrations of a recipient's middle ear, inner ear, semicircular canals, etc., into electrical signals for use the prosthesis.

SUMMARY

In one aspect of the present invention, an implantable hearing prosthesis is provided. The hearing prosthesis comprises a vibrator for generating vibrations; a coupling arm adapted to be attached to an element of a recipient's ear; and a quick-connector comprising a first quick-connector half disposed on the vibrator and a second quick-connector half disposed on the coupling arm, wherein the connector halves are adapted to be releasably mated with one another to secure the coupling arm in relative position to the vibrator.

In another aspect of the present invention, a method of attaching a coupling arm to a vibrator of an implantable hearing prosthesis using a quick-connector, wherein a first quick-connector half is disposed on the vibrator is provided. The method comprises selecting one of a plurality of coupling arms, wherein each of the coupling arms is attached to a second quick-connector half; releasably, manually mating the second quick-connector half with the first quick-connector half disposed on the vibrator to secure the coupling arm in relative position to the vibrator.

In yet another aspect of the invention, an implantable hearing prosthesis kit is provided. The implantable hearing prosthesis kit comprises a vibrator for generating vibrations; a plurality of coupling arm each adapted to be attached to an element of a recipient's ear; a first quick-connector half disposed on the vibrator; and second quick-connector halves disposed on the coupling arm, wherein the second quick-connector halves are adapted to be releasably mated with the first quick-connector half to secure each of the coupling arms in relative position to the vibrator.

BRIEF DESCRIPTION OF THE DRAWINGS

Illustrative embodiments of the present invention are described herein with reference to the accompanying drawings, in which.

DETAILED DESCRIPTION

Aspects of the present invention are generally directed to a hearing prosthesis having a quick-connector configured to mechanically attach a coupling arm to a vibrator. The quick-connector comprises a first quick-connector half disposed on the vibrator, and a second quick-connector half disposed on the coupling arm. The connector halves are adapted to be releasably mated with one another to secure the coupling arm in relative position to the vibrator such that vibration may be delivered from the vibrator to the ear element via the coupling arm. More particularly, the connector halves secure the coupling arm to the vibrator such that one or more of rotation and translation of the coupling arm relative to the vibrator is minimized.

A quick-connector in accordance with embodiments of the present invention may be used to couple a coupling arm to a vibrator without the need for gluing or crimping operations, which may reduce the time of the surgical procedure, reduce the complexity of the procedure, and/or reduce the risk of failure of the coupling between the coupling arm and the vibrator. As such, a user (e.g. a surgeon) may select an appropriate coupling arm during a surgical procedure in view of needs of the recipient, the specific anatomy of the recipient, and the preferences of the user. Also, by eliminating the crimping operation, may reduce the risk of damaging the hearing prosthesis during the crimping operation.

Figure 1:
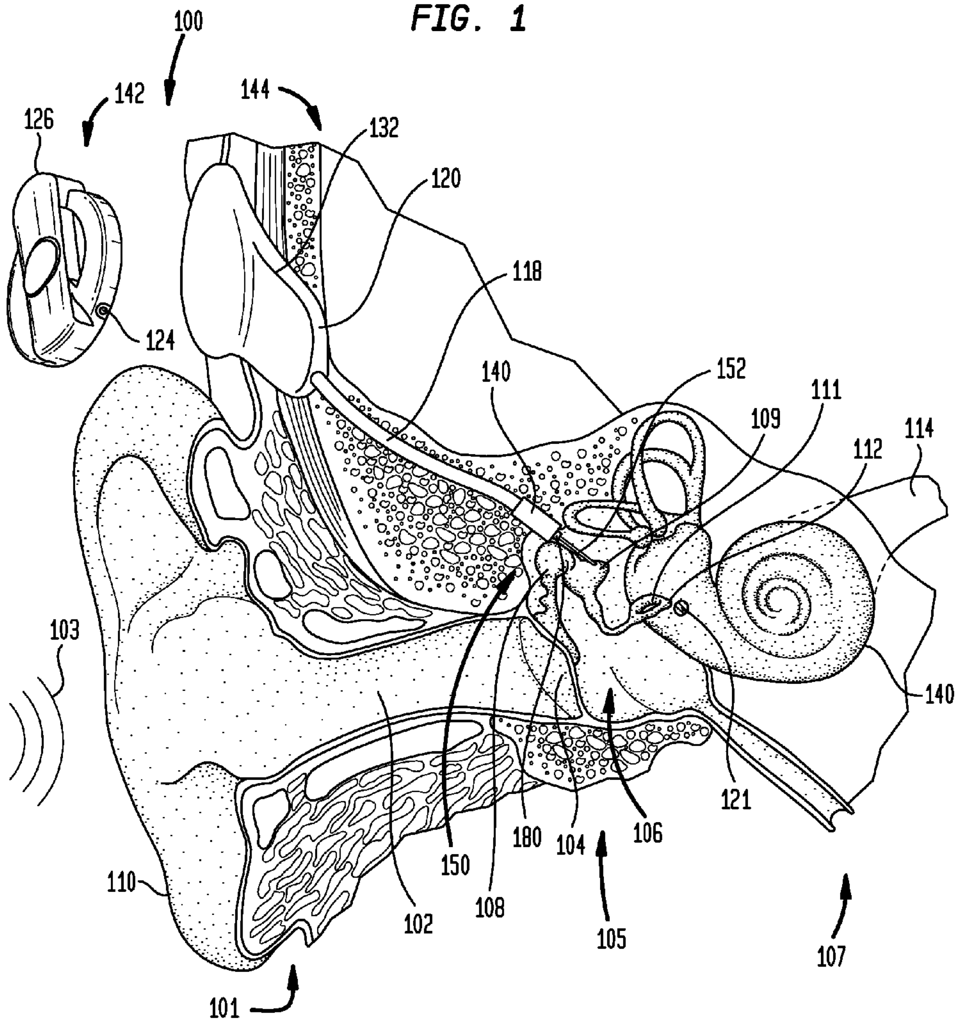
FIG. 1 is a perspective view of a hearing prosthesis having components implanted in a recipient, in accordance with embodiments of the present invention.

FIG. 1 is a perspective view of an exemplary mechanical stimulator 100 having components implanted in a recipient. Elements of the recipient's ear are described below, followed by a description of mechanical stimulator 100.

The recipient's ear comprises an outer ear 101, a middle ear 105 and an inner ear 107. In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown in FIG. 1, mechanical stimulator 100 comprises an external component 142 which is directly or indirectly attached to the body of the recipient, and an internal component 144 that is temporarily or permanently implanted in the recipient. External component 142 typically comprises one or more sound input elements, such as microphones 124 for detecting sound, a sound processing unit 126, a power source (not shown), and an external transmitter unit (not shown). External component 142 shown in FIG. 1 comprises a button processor comprising all the described components, including the external transmitter. It would be appreciated that implementations in which the external coil is a separate component, and the sound processor is a Behind-The-Ear (BTE) device may also be used. The external transmitter unit is disposed on the exterior surface of sound processing unit 126 and comprises an external coil (not shown). Sound processing unit 126 processes the output of microphones 124 and generates encoded signals, sometimes referred to herein as encoded data signals, which are provided to the external transmitter unit. For ease of illustration, sound processing unit 126 is shown detached from the recipient.

Internal component 144 comprises an internal receiver unit 132, a stimulator unit 120, and a stimulation arrangement 150. Internal receiver unit 132 and stimulator unit 120 are hermetically sealed within a biocompatible housing, sometimes collectively referred to herein as a stimulator/receiver unit. Internal receiver unit 132 comprises an internal coil (not shown), and preferably, a magnet (not shown) fixed relative to the internal coil. The external coil transmits electrical signals (i.e., power and stimulation data) to the internal coil via a radio frequency (RF) link. The internal coil is typically a wire antenna coil comprised of multiple turns of electrically insulated single-strand or multi-strand platinum or gold wire. The electrical insulation of the internal coil is provided by a flexible silicone molding (not shown). In use, implantable receiver unit 132 may be positioned in a recess of the temporal bone adjacent auricle 110 of the recipient.

Stimulation arrangement 150 is implanted at least partially in middle ear 105. Stimulation arrangement 150 comprises an actuator module 140 including a vibrator, and a coupling arm 152 attached thereto via a quick-connector 180. As shown, stimulation arrangement 150 is implanted and/or configured such that a portion of coupling arm 152 contacts incus 109. It would be appreciated that in alternative embodiments, stimulation arrangement 150 may comprise another coupling arm 152 configured to contact another portion of the recipient's ear, such as the recipient's stapes 111, round window 121, oval window 112, etc.

As noted above, a sound signal is received by one or more microphones 124, processed by sound processing unit 126, and transmitted as encoded data signals to internal receiver 132. Based on these received signals, stimulator 120 generates drive signals which cause actuation of actuator module 140. This actuation is transferred to coupling arm 152 such that waves of fluid motion of the perilymph within cochlea 140 are generated.

Figure 2:
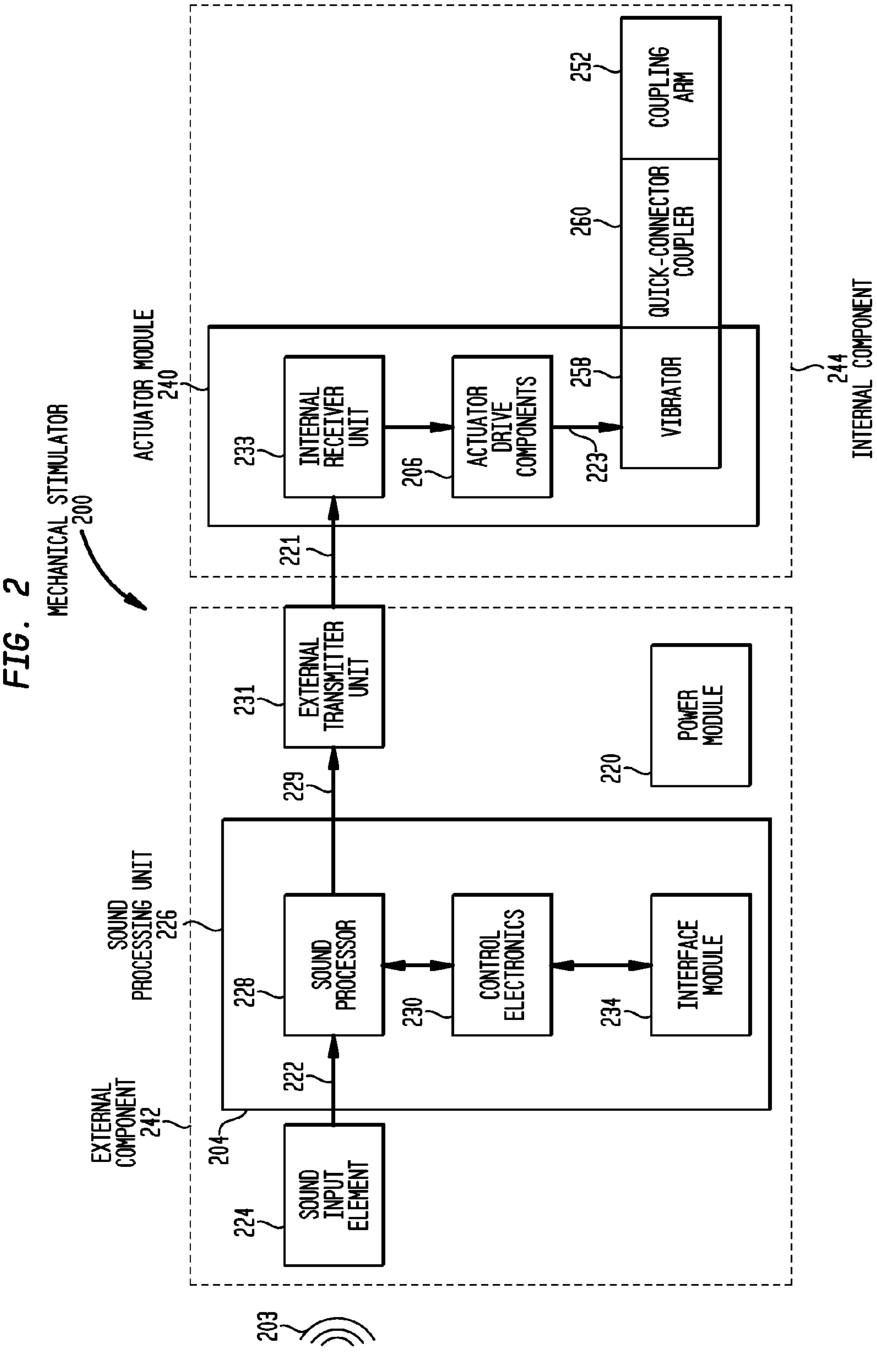
FIG. 2 is a functional block diagram of a hearing prosthesis in accordance with embodiments of the present invention.

FIG. 2 is a functional block diagram of an embodiment of mechanical stimulator 100 of FIG. 1, shown as mechanical stimulator 200. As shown, mechanical stimulator 200 comprises an embodiment of external component 142, referred to herein as external component 242, and an embodiment of internal component 144, referred to herein as internal component 244. External component 242 comprises one or more sound input elements 224, a sound processing unit 226, a power module 220, and an external transmitter unit 231.

Sound input element 224 receives a sound 203 and outputs an electrical signal 222 representing the sound to a sound processor 228 in sound processing unit 226. Sound processor 228 generates encoded signals 229 which are provided to external transmitter unit 231. As should be appreciated, sound processor 228 uses one or more of a plurality of techniques to selectively process, amplify and/or filter electrical signal 222 to generate encoded signals 229. In certain embodiments, sound processor 228 may comprise substantially the same sound processor as is used in an air conduction hearing aid. In further embodiments, sound processor 228 comprises a digital signal processor.

External transmitter unit 231 is configured to transmit the encoded data signals to internal component 244. In certain embodiments, external transmitter unit 231 comprises an external coil which forms part of a radio frequency (RF) link with components of internal component 244. Internal component 244 comprises an embodiment of actuator module 140, referred to herein as actuator module 240. Actuator module 240 comprises an internal receiver unit 233, actuator drive components 206, and an actuator 258 referred to herein as vibrator 258. Internal receiver unit 233 comprises an internal coil which receives power and encoded signals from the external coil in external transmitter unit 231.

The encoded signals 221 received by internal receiver unit 233 are provided to actuator drive components 206. Based on the received signals, actuator drive components 206 output an electrical drive signal 223 to vibrator 258. Based on drive signal 223, vibrator 258 actuates (e.g., vibrates) coupling arm 252 to cause a propagating wave in the perilymph of the recipient's cochlea.

In the embodiment illustrated in FIG. 2, vibrator 258 is mechanically and releasably attached to a coupling arm 252 by a quick-connector 280. As used herein, a quick-connector is a coupler that has first and second halves that may be releasably connected to one another using only manual force (ie. manually deformable) and without permanently altering the physical structure of either of the connector halves. As used herein, manual force is force applied by the hand of an average user either directly or via a manual tool such as manually actuated tweezers.

As described in more detail below, quick-connector 280 secures coupling arm 252 in relative position to vibrator 258.

That is, quick-connector 280 substantially prevents one or more of rotation and lateral translation of coupling arm 252 relative to vibrator 258.

As shown in FIG. 2, sound processing unit 226 further comprises an interface module 234 and control electronics 230. These components may function together to permit a recipient or other user of hearing prosthesis 200 to control or alter the operation of the prosthesis. For example, in certain embodiments of the present invention, based on inputs received by an interface module 234, control electronics 230 may provide instructions to, or request information from, other components of prosthesis 200.

Although the embodiments of FIG. 2 have been described with reference to an external component, it should be appreciated that in alternative embodiments hearing prosthesis 200 is a totally implantable prosthesis. In such embodiments, sound processing unit 226 is implanted in a recipient. In such embodiments, a sound processor may communicate directly with the actuator drive components and the transmitter and receiver may be eliminated.

Figure 3A:
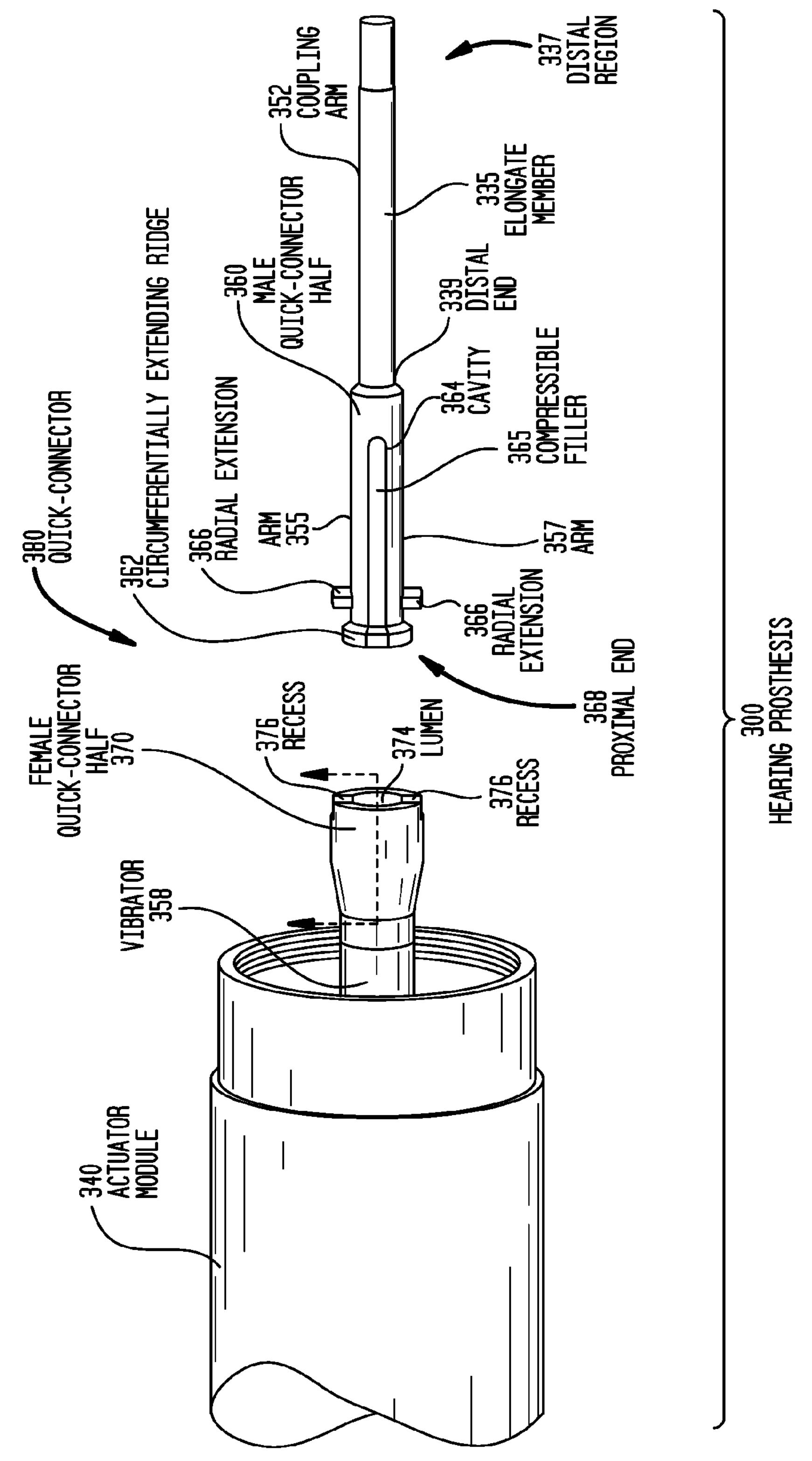
FIG. 3A is a partial perspective view of a mechanical stimulator including a quick-connector in accordance with embodiments of the present invention.

FIG. 3A is a partial perspective view of an embodiment of mechanical stimulator 200 of FIG. 2, shown as mechanical stimulator 300 including a quick-connector 380 in accordance with embodiments of the present invention. Mechanical stimulator 300 includes an actuator module 340, a coupling arm 352 and a quick-connector 380 including a first male quick-connector half 360 and second female quick-connector half 370. Male quick-connector half 360 is attached to or disposed on the proximal end of coupling arm 352, while female quick-connector half 370 is attached to or disposed an end of vibrator 358.

In the embodiments of FIG. 3A, male quick-connector half 360 is a deformable element comprising first and second arms 355 and 357 defining a cavity 364 there between. Cavity 364 is filled with a compressible filler 365. In operation, cavity 364 and compressible filler 365 allow male quick-connector half 360 to be deformed, by the application of manual force, into a compressed configuration (as shown in FIG. 3C) in which the diameter 381 of proximal end 368 of male quick-connector half 360 is temporarily reduced. Male quick-connector half 360 returns to an uncompressed configuration, shown in FIG. 3A, when the manual force is removed. In some embodiments, when the manual force is removed, male quick-connector half 360 is biased so as to return to an uncompressed configuration as a result of the elasticity of one or more of compressible filler 365 and first and second arms 355 and 357. Compressible filler 365 may comprise, for example, silicone or any other substantially elastic material.

Male quick-connector half 360 further comprises a plurality of stabilizing features in the form of one or more circumferentially extending ridges 362 and radial extensions 366. As such, ridges 362 comprise one or more elements disposed at proximal end 368 of male quick-connector half 360 and each extend at least partially around the circumference of half 360. Additionally, in the embodiment illustrated in FIG. 3A., each of first and second arms 355 and 357 comprises one radial extension 366.

In the embodiment shown in FIG. 3A, female quick-connector half 370 includes a lumen 374 having a diameter that is approximately equal to, or smaller than, diameter 381 of proximal end 368 in the uncompressed configuration of quick-connector half 360. More specifically, when male quick-connector half 360 is compressed by manual force into the compressed configuration, the diameter 381 of end 368 is reduced by an amount sufficient for lumen 374 to receive end 368. As such, female quick-connector half 370 receives male quick-connector half 360 into lumen 374 when male quick-connector half 360 is in its compressed configuration.

As shown in FIG. 3A, female quick-connector half 370 also comprises stabilizing features, referred to herein as recesses 372 (shown in FIGS. 3B and 3D) and 376. Recesses 372 and 376 extend radially from lumen 374 of female quick-connector half 370 and configured to mate with radial extensions 366 of male quick-connector half 360. As such, when male and female quick-connector halves 360 and 370 are coupled to one another, the stabilizing features of male and female quick-connector halves 360 and 370 are configured to interoperate to prevent one or more of axial rotation, axial translation and lateral translation of coupling arm 352 relative to vibrator 358. In the embodiment illustrated in FIG. 3A, protrusions 362 are configured to interoperate with recesses 372, and protrusions 366 are configured to interoperate with recesses 376.

In the embodiment illustrated in FIG. 3A, female quick-connector half 370 includes two recesses 376. However, female quick-connector half 370 may comprise any number of recesses 376.

Figure 3B:
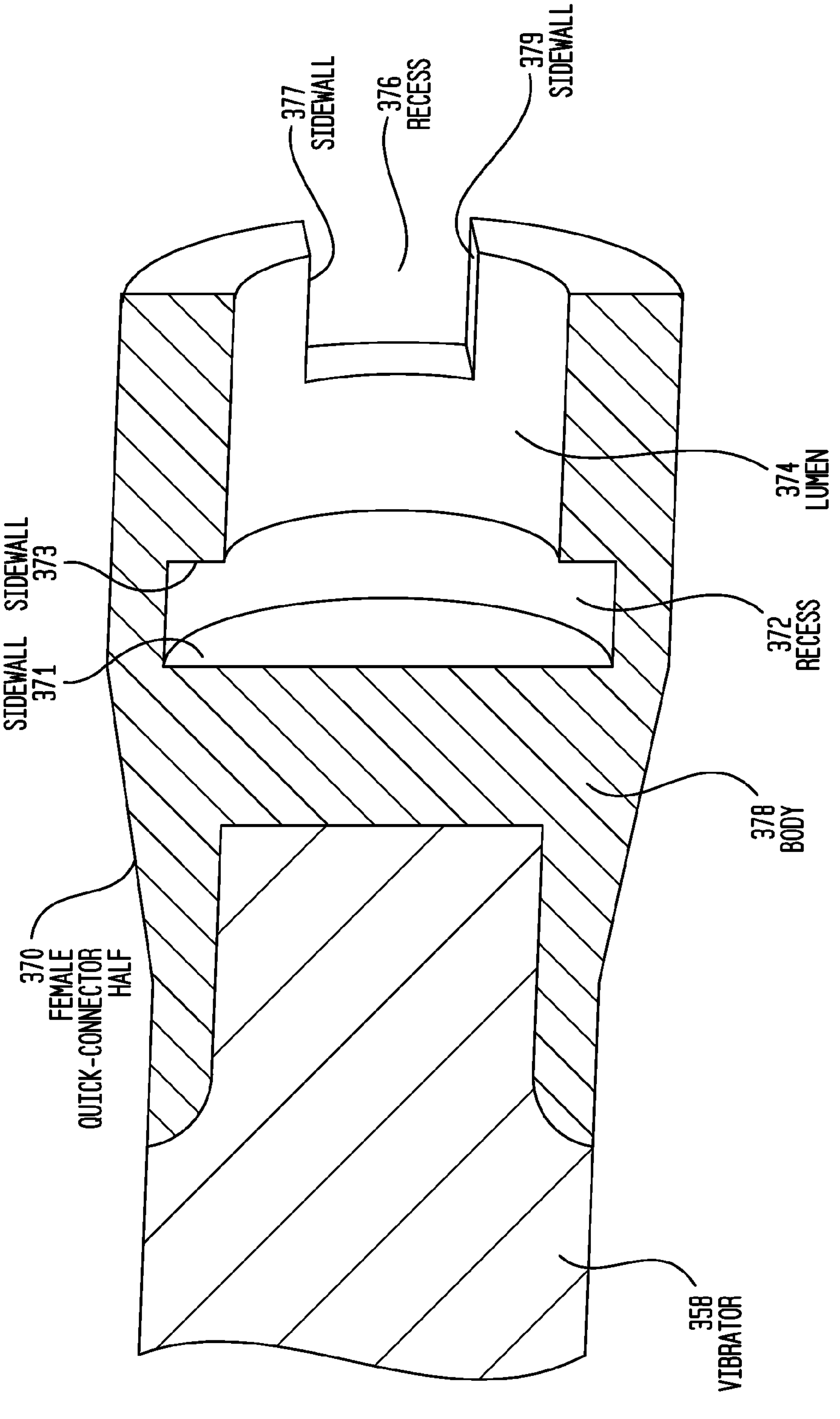
FIG. 3B is a cross-sectional view of female quick-connector half of the quick-connector of FIG. 3A in accordance with embodiments of the present invention.
Figure 3C:
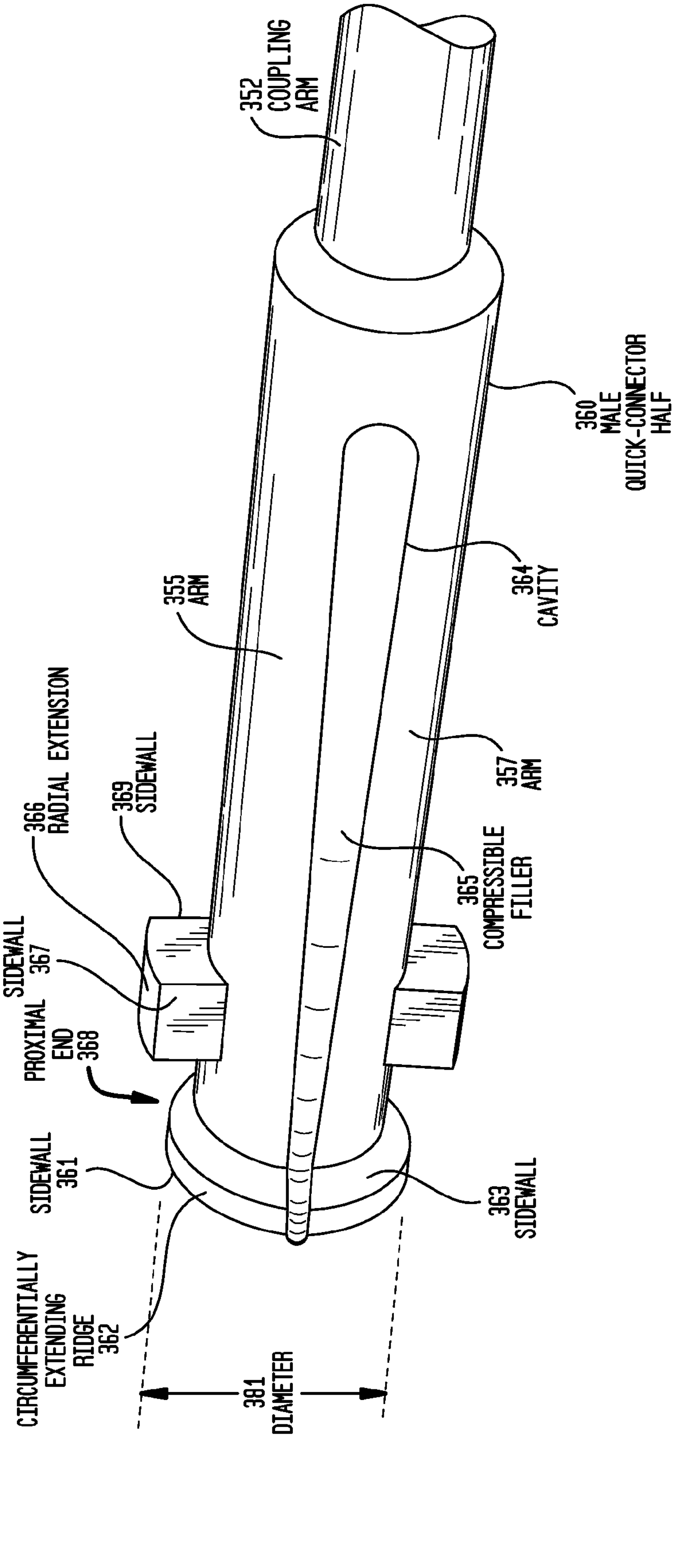
FIG. 3C is a perspective view of male quick-connector half of a quick-connector of FIG. 3A in accordance with embodiments of the present invention.

FIG. 3B is a cross-sectional view of female quick-connector half 370 of FIG. 3A taken along line 3B in FIG. 3A, while FIG. 3C is a perspective view of male quick-connector half 360 of FIG. 3A. As shown, female quick-connector half 370 includes a body 378 disposed on vibrator 358. Body 378 includes lumen 374 and a recess 372 extending radially from the lumen. As illustrated, body 378 includes opposing sidewalls 371 and 373 that partially define recess 372. In addition, body 378 includes a recess 376 that also extends radially from lumen 374. As shown, body 378 includes sidewalls 377 and 379 that partially define recess 376.

In embodiments of the present invention, male quick-connector half 360 may be advanced into lumen 374 until ridge 362 is aligned with recess 372 such that removal of the manual force will cause ridge 362 to move into and mate with recess 372. When ridge 362 is disposed in respective recess 372, recess 372 substantially prevents the movement of protrusions 362 between sidewalls of the recesses 372.

Figure 3D:
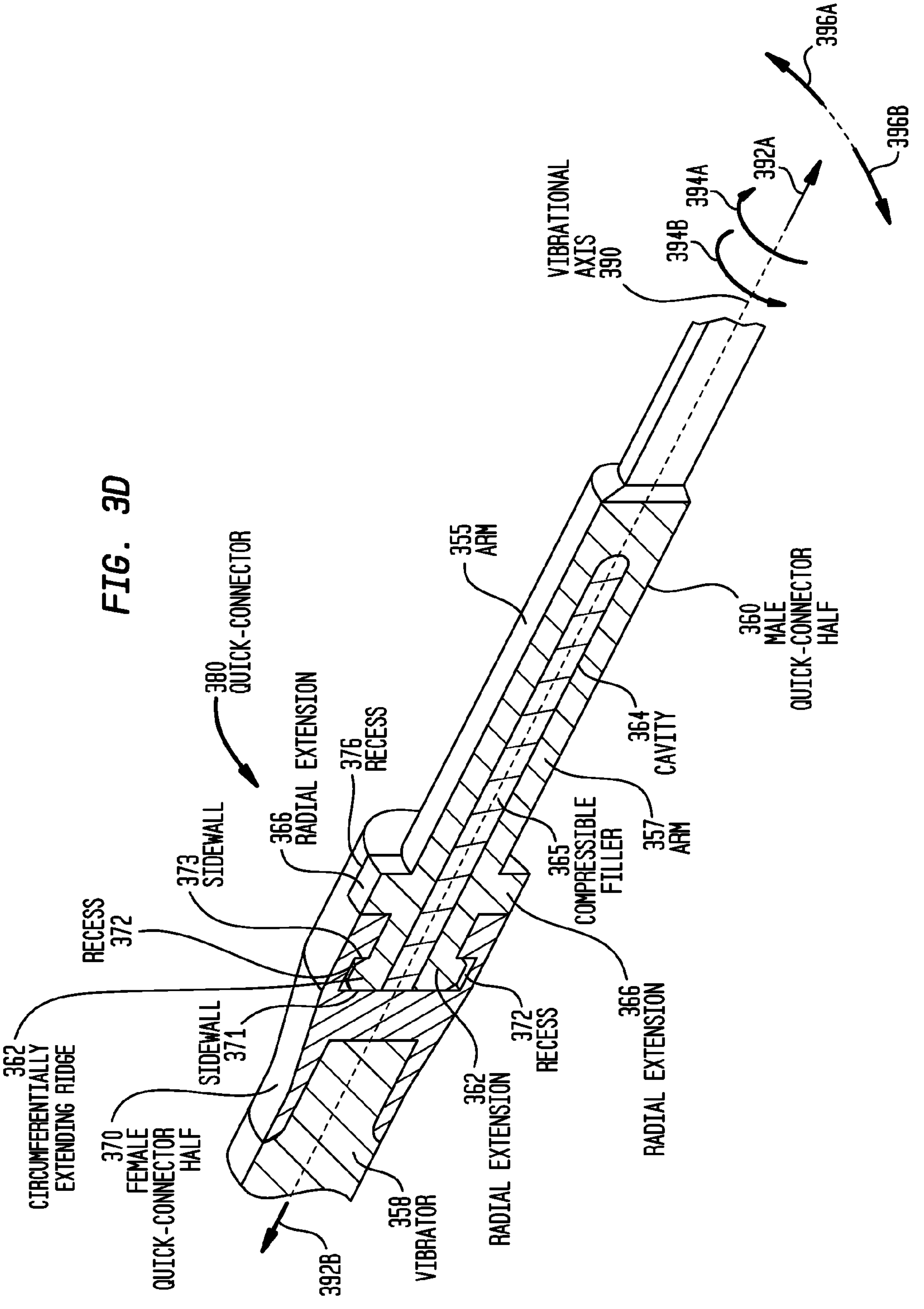
FIG. 3D is a partial cross-sectional view of a mechanical stimualtor including a quick-connector of FIG. 3A in accordance with embodiments of the present invention.

FIG. 3D is a partial cross-sectional view of an implantable hearing prosthesis including quick-connector 380 of FIG. 3A in accordance with embodiments of the present invention. As shown in FIG. 3D, when male and female quick-connector halves 360 and 370 are attached to one another, ridge 362 is disposed in recess 372, and radial extensions 366 are disposed in recesses 367. In certain embodiments of the present invention, vibrator 358, and coupling arm 253, vibrate substantially along vibrational axis 390 in either of the directions shown by arrows 392A and 392B.

As noted above, ridges 362 and recesses 372 interoperate to substantially prevent axial translation of coupling arm 352 relative to vibrator 358. As used herein, "axial translation" refers to movement along the vibrational axis in either of the directions indicated by arrows 392A and 392B. In the embodiment illustrated in FIG. 3D, axial translation of coupling arm 352 relative to vibrator 358 refers to movement of coupling arm 352, relative to vibrator 358, along vibrational axis 390 in either of the directions indicated by arrows 392A and 392B. In certain embodiments of the present invention, radial extensions 362 and recesses 372 are correspondingly dimensioned such that features collectively prevent movement substantial axial translation of coupling arm 352, relative to vibrator 358. In embodiments of the present invention, the walls 371, 372 of recess 372 have a specific angle with regards to the vibrational axis. In this configuration, axial translation is prevented by the combination of: the sidewall 369 (FIG. 3C) of radial extension 366 mating with the sidewall 379 (FIG. 3B) of recess 376, and the angled sidewall 363 mating with sidewall 373. The advantage of the angled sidewall 363 is to compensate for manufacturing spread, caused by dimensional tolerances on the parts. The angle is chosen so that there is a continual contact between the angled sidewall 363 and the corner of sidewall 373 with lumen 374. As such, this may cause male quick-connector half 360 may not reach its uncompressed position again, but without any further problem. This configuration does not need contact between sidewall 371 and sidewall 361.

In certain embodiments of the present invention, radial extensions 366 and recesses 376 interoperate to substantially prevent axial rotation of coupling arm 352 relative to vibrator 358. As used herein, “axial rotation” refers to rotation around the vibrational axis of the vibrator. In the embodiment illustrated in FIG. 3D, axial rotation of coupling arm 352 relative to vibrator 358 refers to the rotation of coupling arm 352, relative to vibrator 358, around vibrational axis 390 in either of the directions indicated by arrows 394A and 394B.

In certain embodiments of the present invention, stabilizing features of male and female quick-connector halves 360 and 370 also interoperate to substantially prevent lateral translation of coupling arm 352 relative to vibrator 358. As used herein, “lateral translation” refers to movement of a component off of an axis such that it is no longer aligned with the axis. For example, in some embodiments of the present invention, lateral translation of coupling arm 352 may refer to movement of coupling arm 352 of off vibrational axis 390 in either of the directions illustrated by arrows 396A and 396B. Arrows 396A and 396B show exemplary directions of lateral translation, and lateral translation, as used herein, also includes the movement of a coupling arm off of the vibrational axis in any other direction.

In the embodiment illustrated in FIGS. 3A-3D, male quick-connector half 360 comprises two ridges 362 and two radial extensions 366. In other embodiments, male quick-connector half 360 may include any combination of ridges 362 and radial extensions 366. In each of these embodiments, female quick-connector half 370 includes one or more recesses 372 and 376 that correspond to the number and respective positions of ridges 362 and radial extensions 366 of male quick-connector half 360.

Figure 4A:
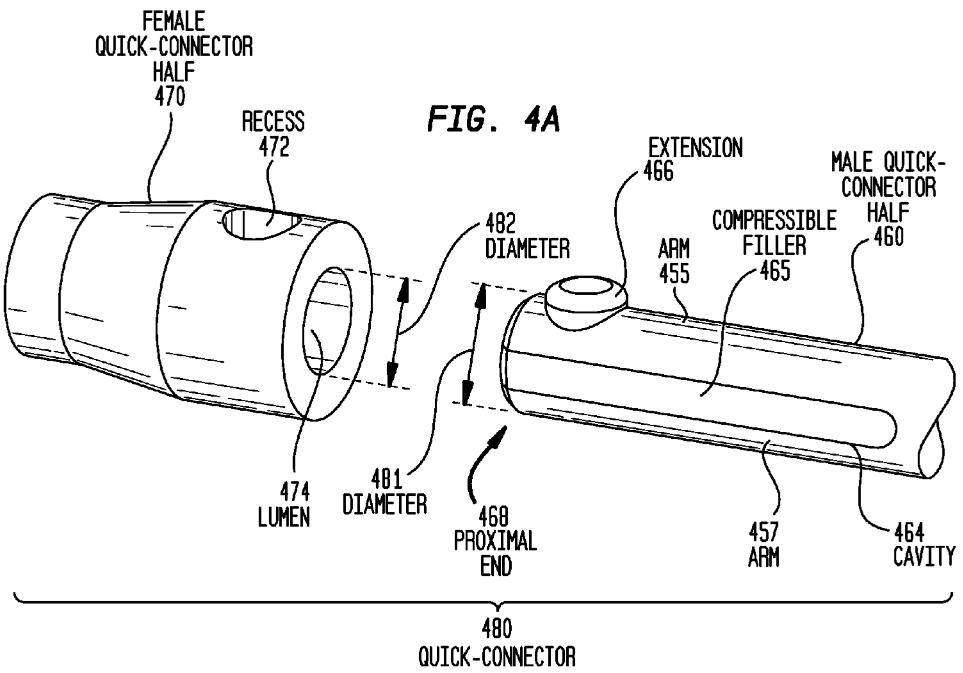
FIG. 4A is a partial perspective view of a quick-connector in accordance with embodiments of the present invention.

FIG. 4A is a partial perspective view of an alternative quick-connector 480. As shown, quick-connector 480 comprises male and female quick-connector halves 460, 4700. Male quick-connector half 460 is attached to or otherwise disposed on a coupling arm (not shown) and female quick-connector half 470 is attached to or otherwise disposed at on a vibrator (not shown).

In the embodiment illustrated in FIG. 4A, male quick-connector half 460 comprises a stabilizing feature, referred to herein as extension 466, and female quick-connector half 470 comprises a corresponding stabilizing feature, referred to herein as recess 472. As shown in FIG. 4A, female quick-connector half 470 includes a lumen 474, and a recess 472 extending radially from the lumen. Male quick-connector half 460 comprises first and second arms 455, 457 defining a cavity 464 filled with a compressible filler 465. Cavity 464 and compressible filler 465 allow male quick-connector half 460 to be compressed, by the application of manual force, into a compressed configuration and to return to an uncompressed configuration, shown in FIG. 4A, when the manual force is removed. In some embodiments, the compressed configuration of male quick-connector half 460 is similar to the compressed configuration of male quick-connector half 360 shown in FIG. 3C.

As shown in FIG. 4A, a diameter 481 of a proximal end 468 of male quick-connector half 460 is, in the uncompressed configuration is greater than, or substantially equal to, the diameter 482 of lumen 474. As such, when male quick-connector half 460 is compressed by manual force into the compressed configuration, diameter 481 is reduced by an amount sufficient for lumen 474 to receive proximal end 468. Upon removal of the manual force male quick-connector half 460 assumes its uncompressed configuration and frictionally engages the inner surfaces of lumen 474.

Figure 4B:
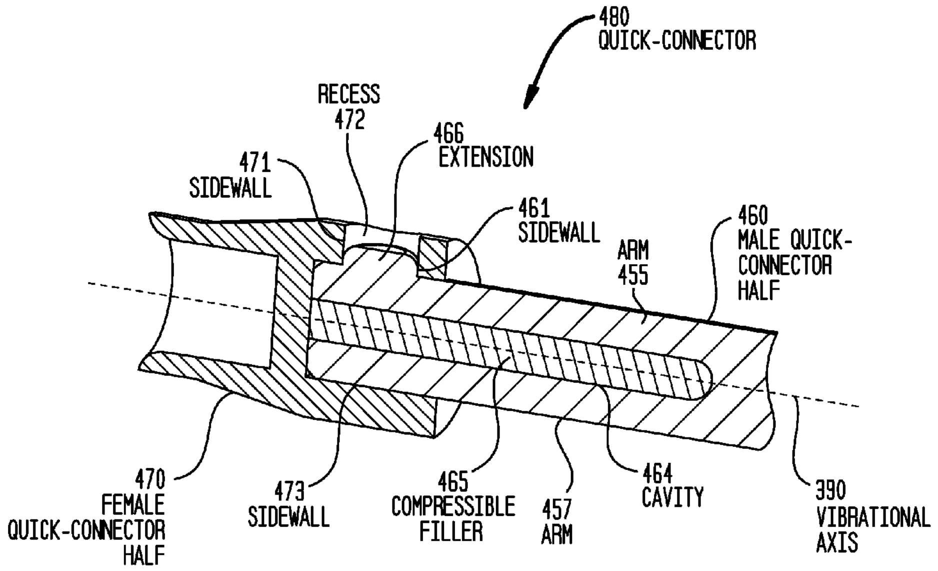
FIG. 4B is a cross-sectional view of the quick-connector FIG. 4A in accordance with embodiments of the present invention.

FIG. 4B is a cross-sectional view of quick-connector 480 of FIG. 4A in a mated or attached arrangement. As shown, when male and female quick-connector halves 460 and 470 are attached to one another, extension 466 is disposed in recess 472. As such, extension 466 and recess 472 interoperate to substantially prevent axial translation of a coupling arm (not shown) connected to male quick-connector half 460 relative to a vibrator (not shown) connected to female quick-connector half 470.

In the embodiments illustrated in FIGS. 4A-4B, recess 472 and extension 466 have corresponding tubular shapes with a circular cross-section. Extension 466 and recess 472 are correspondingly dimensioned such that, when a extension 466 is disposed in a recess 472, sidewall 471 abuts sidewall 461 of extension 466 to substantially prevent movement of extension 466 within recess 472. As such, the abutting surfaces substantially prevents axial translation of the coupling arm and rotation of extension 466. Additionally, arms 455 and 457 interoperate with sidewall 473 to substantially prevent lateral translation of the coupling arm coupled to male quick-connector half 460.

Figure 5A:
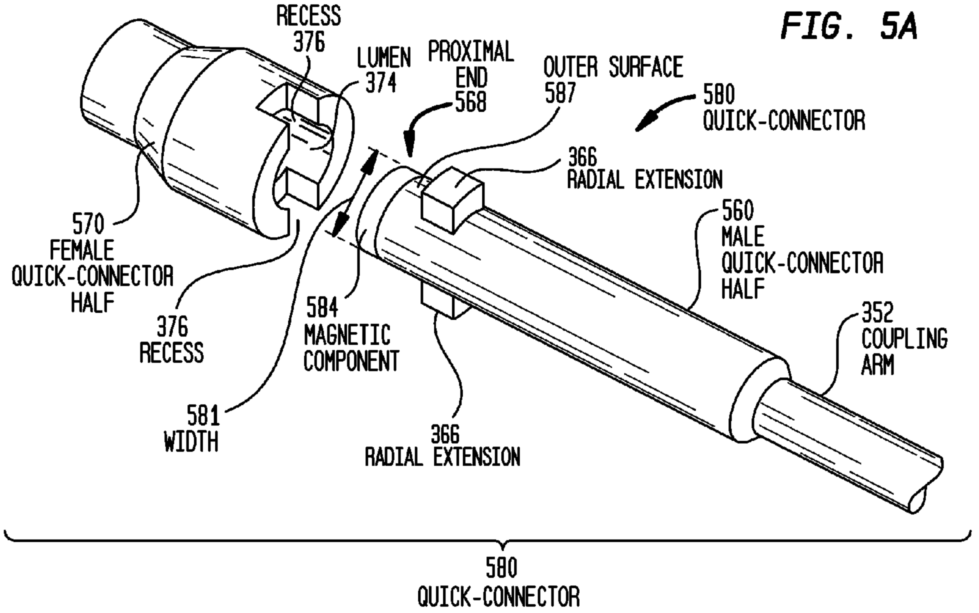
FIG. 5A is a partial perspective view of a quick-connector in accordance with embodiments of the present invention.
Figure 5B:
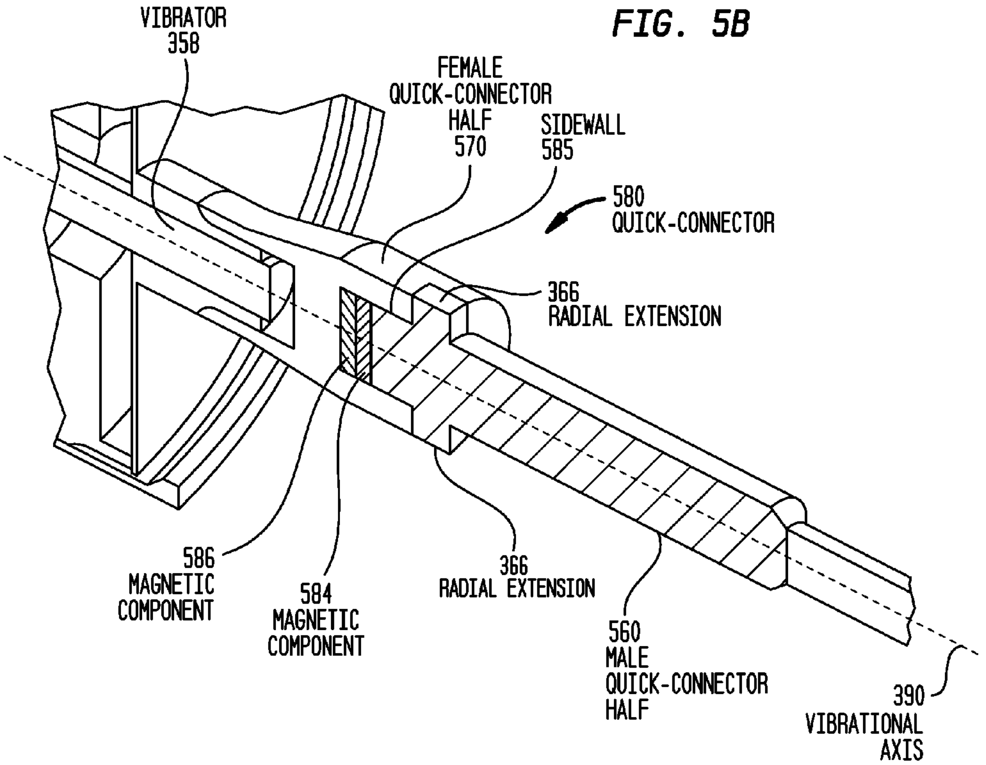
FIG. 5B is a cross-sectional view of the quick-connector FIG. 5A in accordance with embodiments of the present invention.

FIGS. 5A and 5B are perspective and cross-sectional views, respectively, of an embodiment of quick-connector 380 of FIGS. 3A-3D, shown as quick-connector. As shown, quick-connector 580 comprises a male quick-connector half 560 disposed on a coupling arm 352, and a female quick-connector half 570 disposed on a vibrator 358.

Quick-connector half 580 comprises first stabilizing features in the form corresponding radial extensions 366 and recesses 376 as described above with reference to FIGS. 3A-3D. Additionally, quick-connector 580 further comprises second stabilizing features 584, 586. As described below, features 584, 586 each comprise magnetic components.

In the embodiment illustrated in FIGS. 5A-5B, male and female quick-connector halves 560 and 570 are attached to one another by inserting proximal end 568 into lumen 374. When male and female quick-connector halves 560 and 570 are attached, magnetic component 584 is adjacent to magnetic component 586. Magnetic components 584 and 586 are magnetically coupled to one another and interoperate to substantially prevent translation of coupling arm 352 relative to vibrator 358. Magnetic components 584 and 586 may each comprise one or more magnets or magnetic materials.

FIGS. 5A and 5B illustrate the use of two corresponding magnetic components 586, 584, positioned in lumen 374 and at the proximal end 568 of quick-connector half 560. It would be appreciated that other magnetic components may be used on other embodiments of the present invention. In one such embodiment, one or more additional magnetic components are positioned adjacent the outer surfaces of halves 560, 570. These additional magnetic components may further secure halves 560, 570 to one another.

Figure 6A:
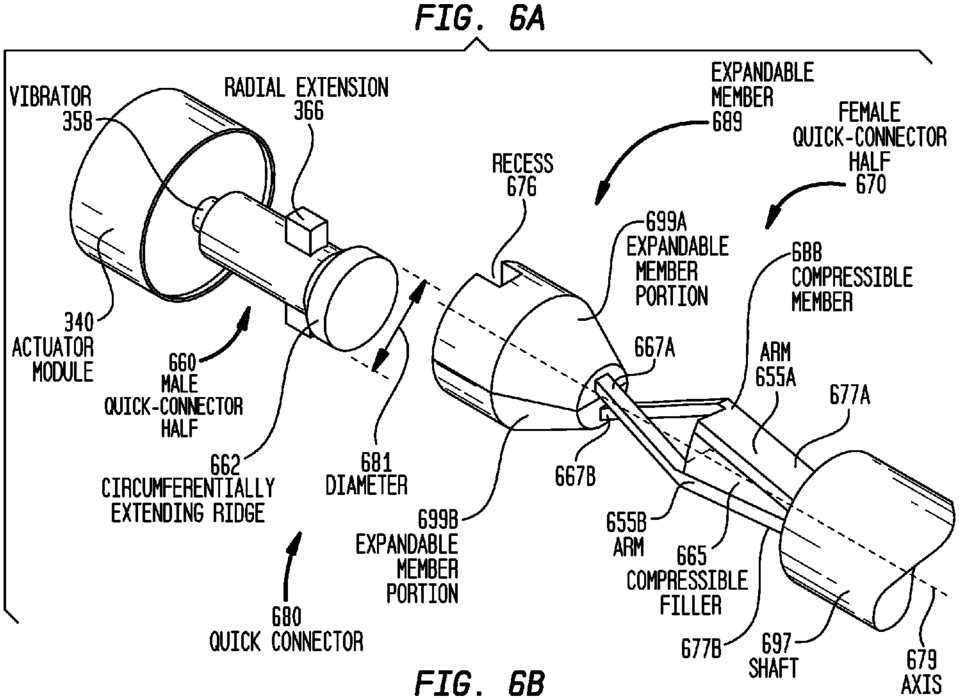
FIGS. 6A and 6B are a partial perspective views of a quick-connector in accordance with embodiments of the present invention.
Figure 6B:
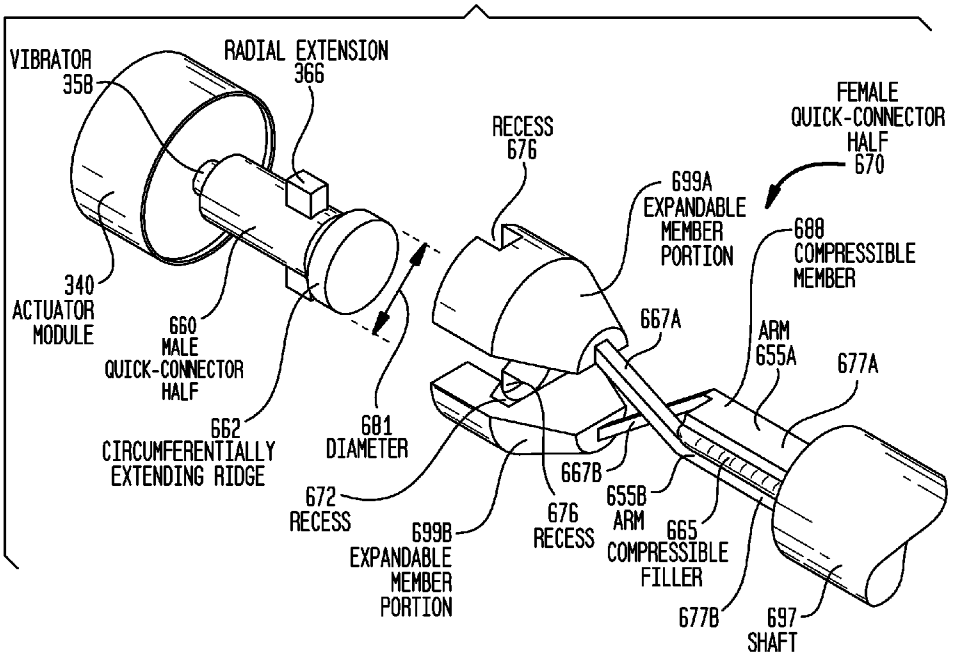
Figure 6C:
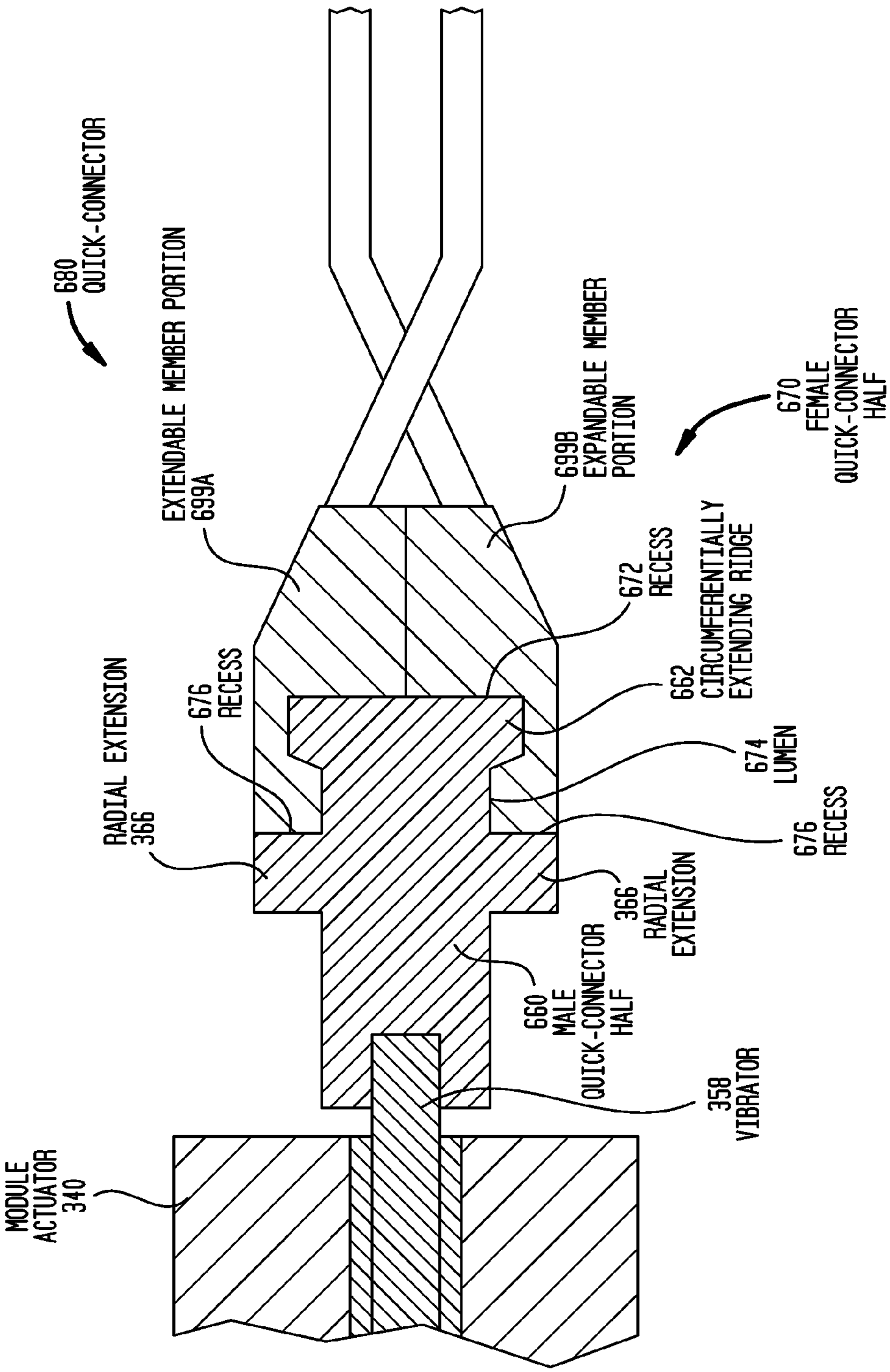
FIG. 6C is a cross-sectional view of the quick-connector of FIGS. 6A and 6B in accordance with embodiments of the present invention.

FIGS. 6A-6C illustrate another embodiment of quick-connector 180, referred to herein as quick-connector 680. Quick-connector 680 comprises a male quick-connector half 660 disposed on a vibrator 358. Similar to male quick-connectors described above, male quick-connector half 660 comprises radial extensions 366 and a circumferentially extending ridge 662.

Quick-connector 680 further comprises a female quick-connector half 670 disposed on a coupling arm (not shown). Female quick-connector half 670 comprises a shaft 697 configured to be attached to the coupling arm. Shaft 697 is connected to an expandable member 689 by a compressible member 688. Compressible member 688 comprises a compressible filler 665 disposed between arms 655. As shown, arms 655 have distal portions 677 that extend from shaft 697 in opposite directions, and proximal portions 667 that extend toward one another and cross the elongate axis 679 of female quick-connector half 670 prior to attaching to expandable member 689. In other words, each arm 655 has proximal and distal portions 667, 677, separated by an obtuse angle. The distal portions 667 are positioned on a first side of axis 679, while proximal portions 667 cross axis 679 so as to attach to portions 699 of expandable member 699 positioned on the opposing side of axis 679 from distal portions 677.

To attach or mate halves 660, 670, a manual force is applied to arms 655, thereby elastically deforming the arms and compressing filler 665. More specifically, in the compressed configuration shown in FIG. 6B, distal portions 677 of arms 655 are compressed towards one another, while proximal portions 667 separate from one another. Because proximal portions 667 are attached to portions 699 of expandable member 689 on opposing sides of axis 679 from distal portions 677, the compression of the distal portions causes portions 699A and 699B of expandable member 689 to separate from one another.

When portions 699 are separate from one another, male quick-connector half 660 is positioned between the portions. Once male quick-connector half 660 is positioned, the manual force may be removed to allow compressible member 688 to assume the uncompressed configuration, shown in FIG. 6A, thereby mating connector halves 660, 670 together.

FIG. 6C is a cross-sectional diagram illustrating connector halves 660, 670 in a mated or attached arrangement. As shown, circumferentially extending ridge 662 is positioned in recess 672, while radial extensions 366 are disposed in recesses 676. Similar to the embodiments described above, the interoperation of ridge 662 and extensions 366 with recesses 672, 676, substantially prevent translation of a coupling arm attached to quick-connector 680.

FIGS. 6A-6C provide an exemplary arrangement for ridge 662, radial extensions 366 and recesses 672, 676. It would be appreciated that other arrangements of one or more ridges, extensions and corresponding recesses are within the scope of the present invention.

In embodiments of the present invention, a quick-connector may be used to removably couple any one of a plurality of coupling arms to vibrator so as to deliver mechanical stimulation to, or receive vibrations from, an element of a recipient's ear. FIGS. 7A-7E illustrate various coupling arms 752 that may be coupled to a vibrator via a quick-connector in embodiments of the present invention. As shown, each of coupling arm 752 has a male quick-connector half 360 as described above with reference to FIGS. 3A-3D disposed on, attached to, or otherwise integrated in its proximal end 739.

Figure 7A:
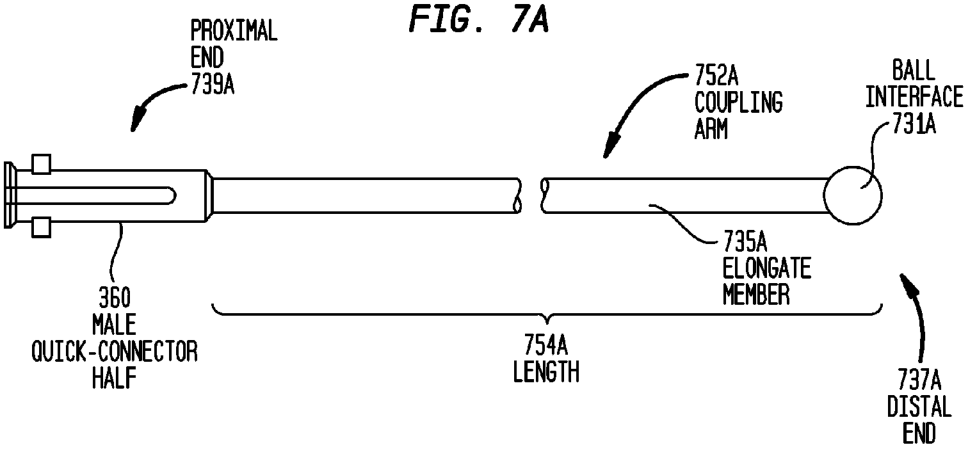
FIGS. 7A-7E illustrate several coupling arms that may be coupled to an actuator of a mechanical stimulator using a quick-connector in accordance with embodiments of the present invention.

As shown in FIG. 7A, a coupling arm 752A comprises an elongate member 735A having a length 754A, a proximal end 739A at which a male quick-connect end 360 is disposed and a distal end 737A at which a ball interface 731A is disposed. In certain embodiments, ball interface 731A is dimensioned to abut a recipient's round window.

Figure 7B:
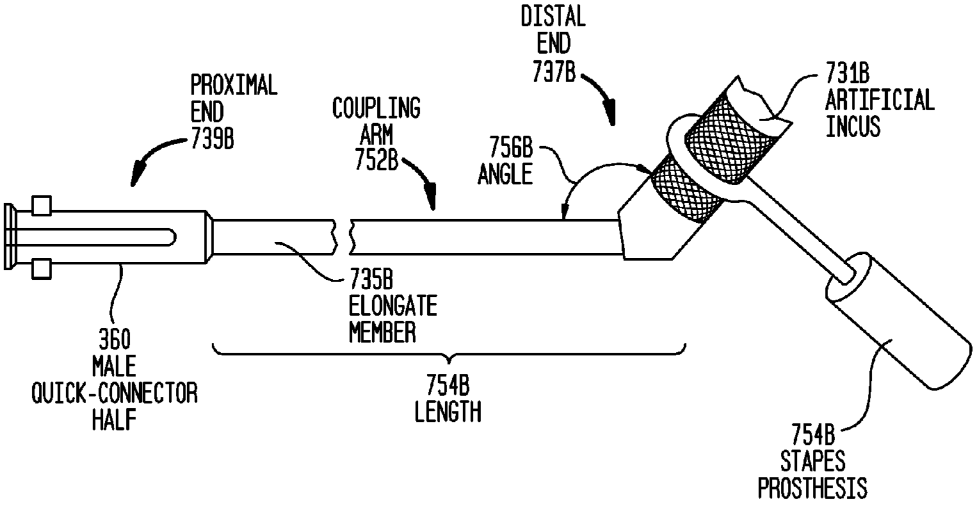

FIG. 7B illustrates a coupling arm 752B comprising an elongate member 735B having a length 754B, and distal end 739B artificial incus 731B and stapes prosthesis 732B are disposed. Artificial incus 731B forms an angle 756B with elongate member 735B, and stapes prosthesis 732B is attached to artificial incus 731B as shown in FIG. 7B. Stapes prosthesis 732B is configured to contact a recipient's oval window, and coupling arm 752B transfers mechanical vibrations from the vibrator to or through the oval window.

Figure 7C:
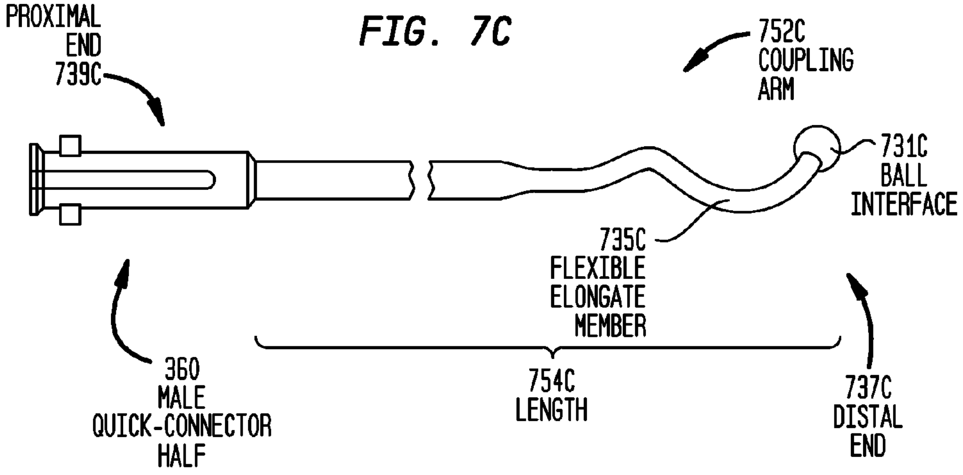

FIG. 7C illustrates a coupling arm 752C comprising a flexible elongate member 735C having a length 754C, and a distal end 737C at which a ball interface 731C is disposed. Ball interface 731C is configured to contact a bone of the recipient's middle ear or a surface of the recipient's inner ear. In certain embodiments, flexible elongate member 735C is a flexible wire.

Figure 7D:
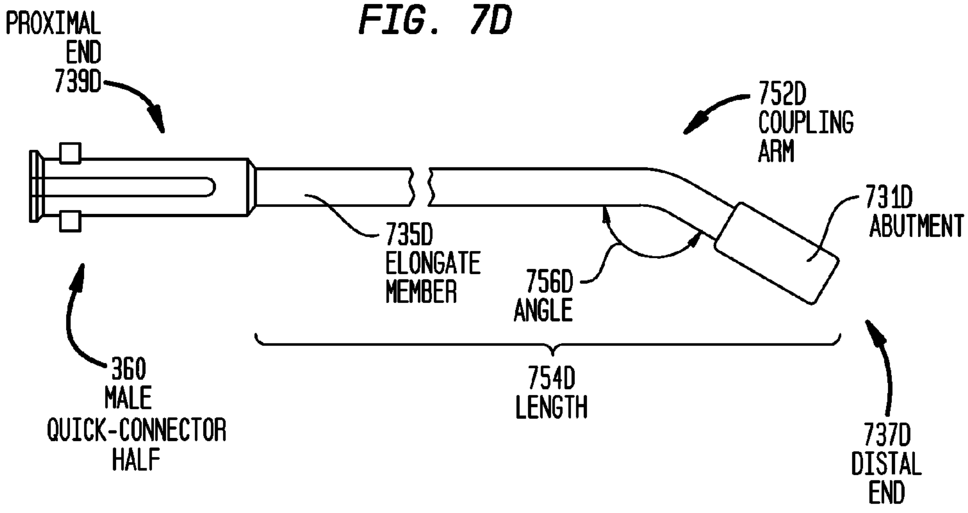

FIG. 7D illustrates a coupling arm 752B comprising an elongate member 735D having a length 754D, and a distal end 737D at which an abutment 731D is disposed. In certain embodiments, elongate member 735D is bent at an angle 756D, and abutment 731D is shaped similar to a portion of a stapes prosthesis. In such an embodiment, coupling arm 752D has a length 754D that extends from the vibrator at its intended implant site to place abutment 731D in contact with the oval window.

Figure 7E:
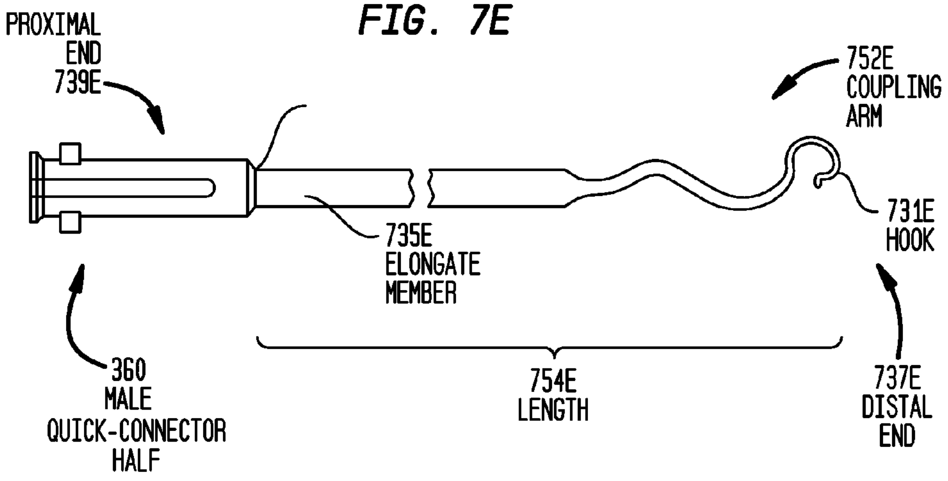

FIG. 7E illustrates a coupling arm 752E comprises an elongate member 735E having a length 754E, and a distal end 737E at which a hook 731E is disposed. Hook 737E is configured to clip onto a recipient's incus. Portions of elongate member 735E are bent to place hook 731E at a desired orientation adjacent to the incus to facilitate coupling.

It would be appreciated that the embodiments of FIGS. 7A-7E are merely illustrative and alternative embodiments are within the scope of the present invention. For example, each coupling arm 752 may include a female quick-connector, any one of the coupling arms described herein may be connected to a vibrator using a quick-connector in accordance with any one of the embodiments described herein. Additionally, coupling arms 752 may different lengths to accommodate the particular recipient and vibrator implant site.

In certain embodiments of the present invention, a kit for a hearing prosthesis may be provided. The kit may include an embodiment of hearing prosthesis 100, and a plurality of different coupling arms. In such embodiments, each of the coupling arms is configured to be coupled to a vibrator of the hearing prosthesis via a quick-connector in accordance with embodiments of the present invention.

Figure 8:
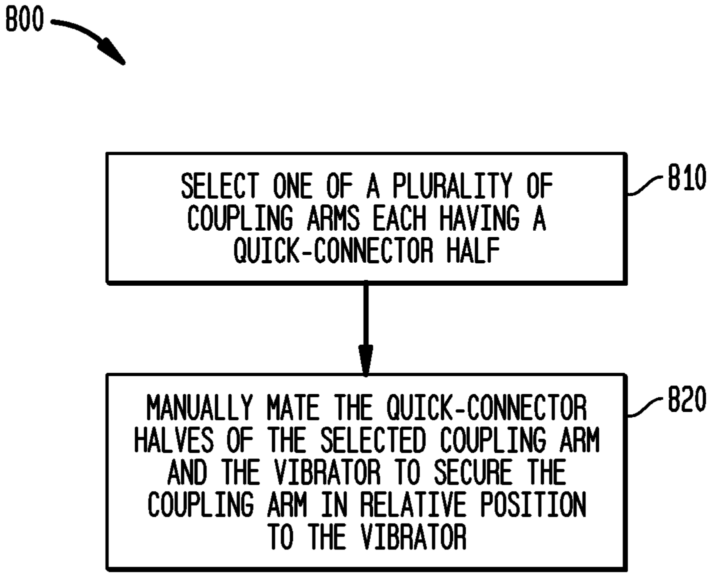
FIG. 8 is a flowchart illustrating a method of coupling a coupling arm to a vibrator of a mechanical stimulator using a quick-connector in accordance with embodiments of the present invention.

FIG. 8 is a flowchart illustrating a process 800 of attaching a coupling arm to a vibrator of a hearing prosthesis using an embodiment of a quick-connector of the present invention. Process 800 begins at block 810 where a coupling arm is selected from a plurality of arms each having a quick-connect half disposed thereon. At block 820, the quick-connector half disposed on the coupling arm is mated with a second quick-connector half disposed on or otherwise attached to a vibrator. The connector halves are mated so as to secure the coupling arm in relative position to the vibrator. Specifically, the halves are mated so as to substantially prevent one or more of axial rotation, axial translation and lateral translation.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. The present embodiments are, therefore, to be considered in all respects as illustrative and not restrictive.

what is claimed is:

1. An implantable hearing prosthesis comprising:

a vibrator for generating vibrations;

a coupling arm adapted to be attached to an element of a recipient's ear; and a quick-connector comprising a first quick-connector half disposed on the vibrator and a second quick-connector half disposed on the coupling arm, wherein:

the quick-connector halves are adapted to be releasably mated with one another to secure the coupling arm in a relative position to the vibrator;

the first quick-connector half comprises a lumen; and the second quick-connector half is manually deformable.

2. The hearing prosthesis of claim 1, wherein the quick-connector halves secure the coupling arm to the vibrator so as to substantially prevent one or more of rotation and translation of the coupling arm relative to the vibrator.

3. The hearing prosthesis of claim 2, wherein the quick-connector halves are further adapted to secure the coupling arm to the vibrator to substantially prevent lateral translation.

4. The hearing prosthesis of claim 1, wherein the second quick-connector half is further adapted to be at least partially inserted into the lumen.

5. The hearing prosthesis of claim 4, wherein the second quick-connector half comprises at least one extension, and wherein the first quick-connector half comprises at least one recess to receive the at least one extension.

6. The hearing prosthesis of claim 5, wherein the second quick-connector half comprises a plurality of extensions.

7. The hearing prosthesis of claim 4, wherein the second quick-connector half comprises one or more circumferentially extending ridges, and wherein the first quick-connector half comprises one or more recesses to receive the more or more ridges.

8. The hearing prosthesis of claim 4, the deformable second quick-connector half comprises:

first and second elongate arms; and a compressible filler disposed between the elongate arms.

9. The hearing prosthesis of claim 1, wherein the hearing prosthesis is a mechanical stimulator.

10. A method of attaching a coupling arm to a vibrator of an implantable hearing prosthesis using a quick-connector, wherein a first quick-connector half comprises a lumen and is disposed on the vibrator, the method comprising:

selecting one of a plurality of coupling arms, wherein each of the coupling arms is attached to a second quick-connector half that is deformable in response to a manual force;

releasably, manually mating the second quick-connector of the selected coupling arm half with the first quick-connector half disposed on the vibrator to secure the selected coupling arm in relative position to the vibrator.

11. The method of claim 10, wherein manually mating the first and second quick-connector halves comprises:

applying a manual force to the second quick-connector half of the selected coupling arm to reduce the cross-sectional shape thereof;

at least partially inserting the second quick-connector half into the lumen; and releasing the manual from the second quick-connector half.

12. An implantable hearing prosthesis kit comprising:

a vibrator for generating vibrations;

a plurality of coupling arms each adapted to be attached to an element of a recipient's ear;

a first quick-connector half disposed on the vibrator, wherein the first quick-connector half comprises a lumen; and a second quick-connector half disposed on the coupling arm, wherein the second quick-connector is adapted to be manually deformable and releasably mated with the first quick-connector half to secure each of the coupling arms in relative position to the vibrator.

13. The kit of claim 12, wherein each of the plurality of coupling arms comprises an elongate member having an end attached to the second quick-connector half, and wherein the coupling arms differ from one another in one or more characteristics selected from the group comprising:

the length of the elongate member;

the shape of the elongate member;

the flexibility of the elongate member;

an interface feature disposed at the second end of the elongate member; and an angle between the interface feature and the elongate member.

14. The kit of claim 12, wherein the first and second quick-connector halves secure the coupling arm to the vibrator so as to substantially prevent one or more of rotation and translation of the coupling arm relative to the vibrator.

15. The kit of claim 12, wherein the second quick-connector half is further adapted so as to be at least partially inserted into the lumen.

16. The kit of claim 15, wherein the second quick-connector half comprises at least one extension, and wherein the first quick-connector half comprises at least one recess to receive the at least one extension.

17. The kit of claim 15, wherein the second quick-connector half comprises one or more circumferentially extending ridges, and wherein the first quick-connector half comprises one or more recesses to receive the more or more ridges.

* * * * *